United States Patent [19]
Mukae et al.

[11] 4,023,022
[45] May 10, 1977

[54] SYSTEM FOR AUTOMATICALLY AND CONTINUOUSLY MEASURING ZINC AND SULFURIC ACID CONCENTRATION IN CIRCULATING ELECTROLYTE

[75] Inventors: Satoshi Mukae; Kiyosi Yokokawa, both of Shimonoseki, Japan

[73] Assignee: Mitsui Mining & Smelting Co., Ltd., Tokyo, Japan

[22] Filed: July 22, 1975

[21] Appl. No.: 598,032

[30] Foreign Application Priority Data

Aug. 5, 1974 Japan .............................. 49-89582
Aug. 20, 1974 Japan ......................... 49-99431[U]

[52] U.S. Cl. ...................... 235/151.35; 23/253 R
[51] Int. Cl.$^2$ ............... G01N 27/56; G01N 33/20; G06F 15/20
[58] Field of Search ............. 235/151.35; 23/230 R, 23/253 R; 204/242

[56] References Cited
UNITED STATES PATENTS

| | | | |
|---|---|---|---|
| 3,527,566 | 9/1970 | Glassbrook | 23/230 R |
| 3,704,097 | 11/1972 | Capuano | 235/151.35 X |
| 3,811,841 | 5/1974 | Kassel | 23/253 R |
| 3,834,873 | 9/1974 | Picker | 23/230 R |
| 3,904,365 | 9/1975 | Larson et al. | 23/230 R |

Primary Examiner—Edward J. Wise

[57] ABSTRACT

A system for automatically and continuously measuring the zinc and sulfuric acid concentration in an electrolyte circulating through electrolysis cells of a hydrometallurgical zinc production system, in which an inductive solution analyzer capable of continuously detecting the conductivity of the circulating electrolyte is used with a measuring cell disposed in the path of a continuous stream of the circulating electrolyte. The measuring cell comprises a defoaming chamber, a measuring chamber and an overflow chamber, and the continuous stream of the electrolyte flows through the measuring chamber as a downward stream so that bubbles can be removed and precipitation of slurry can be prevented. The signal representative of the detected conductivity is applied to an electronic computer which computes automatically the zinc and sulfuric acid concentration according to predetermined calculation formulas.

4 Claims, 7 Drawing Figures

SYSTEM FOR AUTOMATICALLY AND CONTINUOUSLY MEASURING ZINC AND SULFURIC ACID CONCENTRATION IN CIRCULATING ELECTROLYTE

BACKGROUND OF THE INVENTION

In an electrolysis section of a hydrometallurgical zinc production system, a neutral solution leached and purified in a leaching section and purification section is mixed with a spent electrolyte to prepare an electrolyte of required composition, and this electrolyte is then subjected to electrolysis to cause deposition of metallic zinc on the cathodes so as to recover this electrolytic zinc. The zinc concentration in the electrolyte is gradually reduced with the progress of the electrolysis, and therefore, a purified fresh neutral leaching solution must be supplied to the electrolysis cells. According to common practice, after electrolysis, a predetermined amount of the electrolyte is sent to the leaching section, and a purified fresh leaching solution in an amount corresponding to the above amount of the electrolyte is mixed with the remaining part of the electrolyte when the zinc concentration in the electrolyte is reduced to less than a predetermined setting. The fresh electrolyte is circulated through electrolysis cells. This method is called of preparation of electrolyte.

FIG. 1 shows schematically the process of preparation of electrolyte.

In the hydrometallurgical production of zinc, measurement of the zinc concentration in the circulating electrolyte is thus an important part of the electrolytic process. Automatic measurement of the zinc concentration in the electrolyte circulating through the cells can be attained by means as an on-stream fluorescence X-ray analyzer. However, employment of such a fluorescence X-ray analyzer involves various problems. For example, in the first place, this analyzer cannot be easily installed on the site of measurement due to the fact that it requires a bulky analyzing chamber. Secondly, great care must be given to the safety of operators due to the necessity for provision of a high-voltage power supply and in order to avoid the danger of exposure to the X-rays. Thirdly, the X-ray tube must be periodically replaced by new one resulting in troublesome maintenance and other operating problems. Fourthly, the equipment required for analysis is quite expensive such that it is not acceptable from the economical point of view. Due to various limitations as above described, the fluorescence X-ray analyzer is not commonly widely used.

As is commonly known, an instrument for measuring the sulfuric acid concentration is used in sulfuric acid plants for the purpose of automatic measurement of the sulfuric acid concentration. However, due to the fact that a platinum electrode is employed in this instrument, metals including zinc tend to deposit on the platinum electrode resulting in extreme fouling of the electrode. Thus, reliable measurement is difficult to attain when such instrument is used for measurement of the sulfuric acid concentration in the circulating electrolyte presently discussed.

An inductive solution analyzer is widely employed for the purpose of solution analysis since it has the advantage of ease of maintenance. However this inductive solution analyzer is not directly applicable to the desired automatic measurement of, for example, the zinc concentration in the circulating electrolyte due to the fact that the concentration value must be computed on the basis of an approximate expression. This concentration computation on the basis of such an approximate expression must be automatically carried out in order to attain the desired automatic measurement of the zinc concentration in the circulating electrolyte. Further, undesirable deposition of slurry on the transmitter of the inductive solution analyzer as well as objectionable instrusion of bubbles into this transmitter must be prevented in order that the zinc concentration in the circulating electrolyte can be continuously, automatically and reliably measured. For the above reasons, the desired continuous and automatic measurement of the zinc concentration in the circulating electrolyte by the inductive solution analyzer has not yet been put into practical use.

One form of prior art inductive solution analyzers having a transmitter of bypass type is shown in FIG. 2. Referring to FIG. 2, the transformer portion of the transmitter of the inductive solution analyzer is disposed in a measuring cell 3 which has an inlet port 1 at the bottom thereof and an outlet port 2 at one side thereof. Thus, this measuring cell 3 is of the type in which a solution subject to measurement flows upward therethrough. However, utilization of such type of measuring cell for the measurement of the zinc concentration in the circulating electrolyte results frequently in such a trouble that slurry and bubbles tending to give rise to errors of measurement deposit on and attach to the transformer portion of the transmitter. This is attributable to the structure of the measuring cell in the prior art inductive solution analyzer. More precisely, in this measuring cell, the solution subject to measurement, that is, in this case, the circulating electrolyte flows upward from the inlet port at the bottom toward the outlet port, tending to cause precipitation of slurry toward the bottom. Due to the fact that the inner diameter of the measuring cell is considerably greater than that of the inlet and outlet ports, the velocity of the circulating electrolyte is low in the measuring cell, and the slurry concentration in the circulating electrolyte is gradually increased in the vicinity of the transmitter thereby giving rise to deposition of the slurry on the wall of the liquid passage in the transformer portion of the transmitter. Further, many bubbles included in the circulating electrolyte tend to attach to the wall of the liquid passage in the transformer portion of the transmitter. Therefore the inductive solution analyzer of this kind has been unable to continuously and reliably measure the zinc concentration in the electrolyte circulating through the electrolysis cells. However, for the purpose of automation of the electolytic production of zinc, automation of the measurement of the zinc concentration in the electrolyte circulating through the electrolysis cells in indispensable, and realization of this automatic measurement has been strongly demanded.

SUMMARY OF THE INVENTION

It is an object of the present invention to provide a novel and improved system which is capable of continuously and automatically measuring the zinc and sulfuric acid concentration in a circulating electrolyte of the kind as above described by continuously detecting the conductivity of the circulating electrolyte by an inductive solution analyzer while preventing such a trouble that slurry and bubbles in the circulating electrolyte flowing through a measuring cell deposit on and attach to the transmitter of the inductive solution analyzer.

In accordance with one aspect of the present invention, there is provided a system for automatically and continuously measuring the zinc and sulfuric acid concentration in an electrolyte circulating through an electrolysis cells of a hydrometallurgical zinc production process said measuring system comprising an inductive solution analyzer having a transmitter and capable of continuously detecting the conductivity of the circulating electrolyte, and a measuring cell disposed in the path of a continuous stream of the circulating electrolyte, said measuring cell comprising a defoaming chamber, a measuring chamber and an overflow chamber defined therein by a partition wall, said transmitter of said inductive solution analyzer being disposed within said measuring chamber, an overflow port formed in an upper portion of said partition wall and a first communication port bored in a middle portion of said partition wall to provide communication means between said defoaming chamber and said measuring chamber, and a second communication port bored in a lower portion of said partition wall to provide a communication means between sad measuring chamber and said overflow chamber, whereby the ciruclation electrolyte can always flow through said measuring cell as a downward stream.

Another object of the present invention is to provide an automatic and continuous measuring system of the kind above described in which the conductivity detected continuously by the inductive solution analyzer is used as a parameter so that the zinc and sulfuric acid concentration in the circulating electrolyte can be automatically computed on the basis of predetermined approximate expressions.

In accordance with another aspect of the present invention, there is provided an automatic and continuous measuring system of the above character, wherein the signal representative of the conductivity detected continuously by said inductive solution analyzer is applied through an analog-digital converter to an electronic computer, and said electronic computer computes automatically the zinc and sulfuric acid concentration in the circulating electrolyte on the basis of predetermined approximate expressions given by $$x = A \cdot \delta \, B \cdot [t - Zn] + C$$

$$y = D \cdot \delta + E \cdot [t - Zn] + F$$

where $x$ is the zinc concentration in the circulating electrolyte, $y$ is the sulfuric acid concentration in the circulating electrolyte, $\delta$ is the detected conductivity of the circulating electrolyte, A to F are constants, and $[t - Zn]$ is the total zinc concentration in the circulating electrolyte.

DETAILED DESCRIPTION OF THE INVENTION

Figure 1:
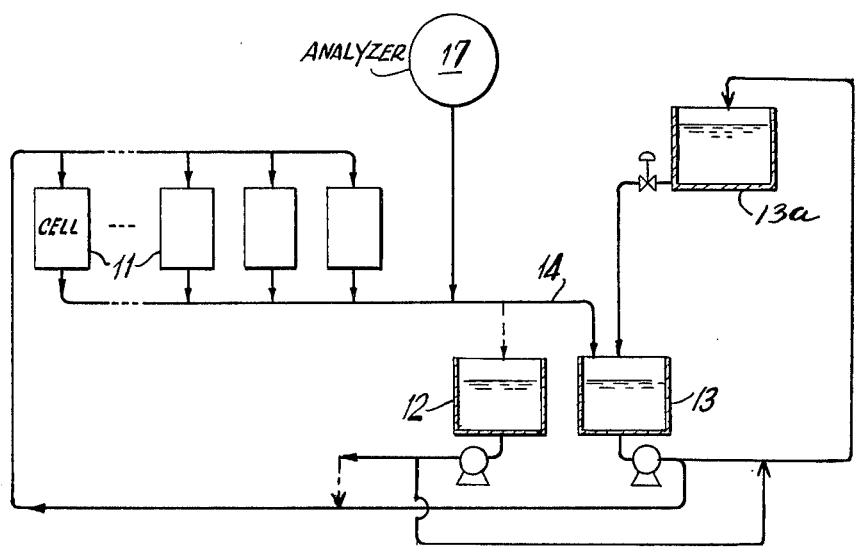
FIG. 1 is a diagrammatic view showing schematically an electrolytic section for obtaining electrolytic zinc.

Referring to FIG. 1 showing an electrolytic section for obtaining electrolytic zinc, a spent electrolyte or circulating electrolyte is sent to be fed through a conduit 14 into circulating tanks 12 and 13 from electrolysis cells. A part of the spent electrolyte in the tanks 12 and 13 is fed to a leaching section 13a, while a purified fresh neutral leaching solution in an amount corresponding to the amount of the spent electrolyte fed to the leaching section is supplied from the leaching section to be mixed with the remaining part of the spent electrolyte to prepare a fresh electrolyte. This fresh electrolyte is recirculated to the electrolyte cells 11 to be subjected to the electrolysis.

Figure 3:
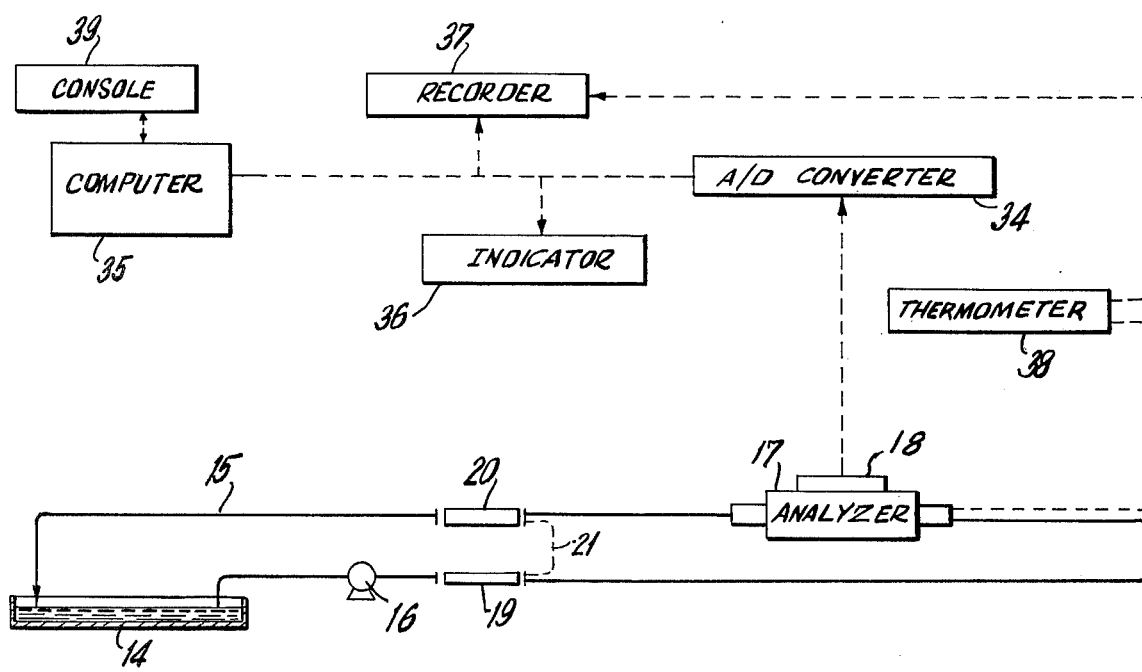
FIG. 3 is a block diagram of an embodiment of the automatic and continuous measuring system according to the present invention.
Figure 2:
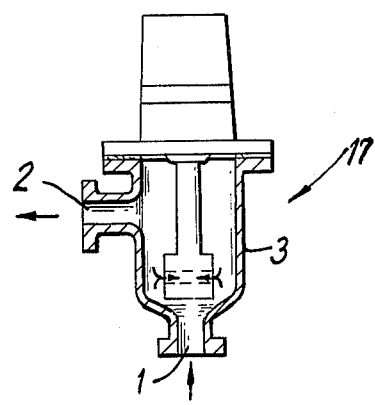
FIG. 2 is a sectional view of a prior art inductive solution analyzer combined with a measuring cell of up-flow type.

Referring to FIGS. 2 and 3, a bypass conduit 15 is branched from the conduit 14 leading from the cells 11 to the circulating tanks 12 and 13. A pump 16 is disposed in this bypass conduit 15 for the drawing part of the circulating electrolyte from the conduit 14, and an inductive solution analyzer 17 is also disposed in this bypass conduit 15 for the purpose of zinc and sulfuric acid concentration measurement. This inductive solution analyzer 17 is partly housed within a meauring cell 18 through which the circulating electrolyte pumped by the pump 16 flows continuously so that the zinc and sulfuric acid concentration therein can be measured. In order to prevent errors in the measured values due to flow of external current to the measuring cell 18, means for removing such external current is provided in the bypass conduit 15. This external removing means includes a pair of graphite pipes 19 and 20 which are disposed on the upstream and downstream sides respectively of the measuring cell 18 and are interconnected by a lead 21 so as to short-circuit the external current. Of course, such means is unnecessary when there is utterly no possibility of appearance of external current. These graphite pipes 19 and 20 made of any suitable material which is electrically conductive and corrosion resistive. In this manner, a part of the circulating electrolyte pumped by the pump 16 from the conduit 14 is fed into the bypass conduit 15 to be supplied into the measuring cell 18 via the graphite pipe 19.

Figure 4:
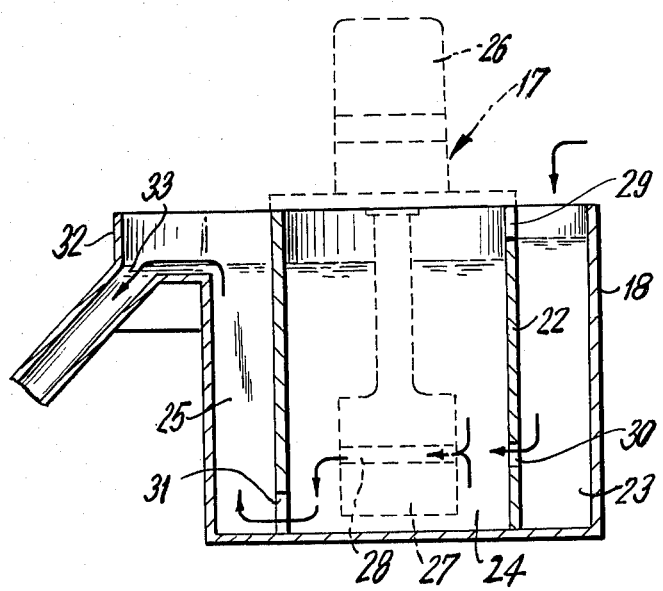
FIG. 4 is a sectional view of a measuring cell employed in the present invention.
Figure 5:
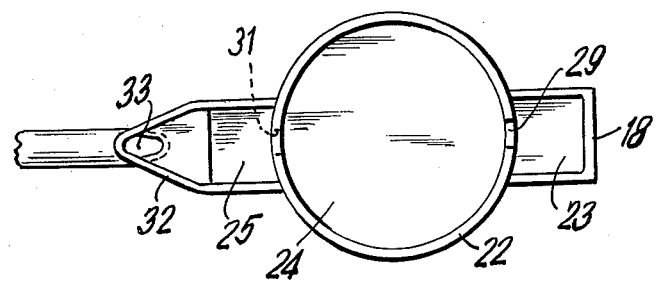
FIG. 5 is a plan view of the measuring cell shown in FIG. 4.

Referring to FIGS. 4 and 5, the interior of the measuring cell 18 is divided into a defoaming chamber 23, a measuring chamber 24 and an overflow chamber 25 by a partition wall 22. The measuring chamber 24 is cylindrical in shape, and a transformer portion 27 of a transmitter 26 of the inductive solution analyzer 17 is disposed within this measuring chamber 24. A central hole or liquid passage 28 extends substantially horizontally through the transformer portion 27 to permit flow of the circulating electrolyte therethrough. The defoaming chamber 23 communicates with the central measuring chamber 24 through an overflow port 29 and a communication port 30 bored in the portion of the partition wall 22 lying between the defoaming chamber 23 and the measuring chamber 24. The overflow port 29 is disposed at the liquid level in the defoaming chamber 23, while the communication port 30 is disposed at substantially a middle portion of the partition wall 22. The central measuring chamber 24 communicates with the overflow chamber 25 through another communication port 31 bored in the portion of the partition wall 22 lying between the measuring chamber 24 and the overflow chamber 25. This communication port 31 is disposed beneath the overflow port 29 and communication port 30, that is, at the bottom portion of the partition wall 22. A discharge port 33 is provided in the outer wall 32 of the overflow chamber 25 at the liquid level in the overflow chamber 25.

The circulating electrolyte flows initially into the defoaming chamber 23 in which bubbles included in the electrolyte are removed so as to prevent intrusion of objectionable bubbles into the passage 28 in the transformer portion 27 of the transmitter 26. Further, the circulating electrolyte would not overflow from the measuring cell 18 by virtue of the provision of the overflow port 29. The circulating electrolyte flows then into the measuring chamber 24 through the communication port 30, and a part of the electrolyte passes through the passage 28 to flow toward and into the overflow chamber 25. Due to the fact that the communication port 31 is situated beneath the communication port 30, the circulating electolyte flows always downward or in the same direction as the direction of precipitation of slurry. Therefore, the slurry in gradually carried by the stream toward the communication port 31 and thus would not deposit on the wall of the passage 28 in the transformer portion 27. It is thus possible to carry out continuous concentration with high precision. The circulating electrolyte is finally discharged to the exterior from the overflow chamber 25 of the measuring cell 18 through the discharge port 33 to be returned to the conduit 14 via the graphite pipe 20 connected in the bypass conduit 15.

The conductivity of the circulating electrolyte flowing continuously through the measuring cell 18 is detected by the inductive solution analyzer 17 according to the measuring principle commonly known in the art. The inductive solution analyzer 17 is shown provided with a by pass type transmitter. It is apparent however that the transmitter may be of the immersed type. The inductive solution analyzer 17 employed in the present invention has, for example, the following detecting characteristics : (i) output : DC 4mA – 20mA, ii) measuring range : 0.2V/cm – 0.5 V/cm at 40° C, iii) temperature compensation : 40° C ± 10° C. A thermistor thermometer is incorporated in the transmitter 26 to detect the temperature of the electrolyte for compensating the temperature on the basis of the result of detection. The temperature coefficient is about 0.005V/cm°C.

An electronic computer 35 is connected to the inductive solution analyzer 17 through an analog-digital converter 34 as shown in FIG. 3. This converter 34 must be selected to suit the specific inductive solution analyzer 17. When the inductive solution analyzer 17 has, for example, the detecting characteristics above specified, the analog-digital converter 34 may have the following characteristics : (i) temperature compensation : temperature setting ± 10° C, (ii) ambient temperature : 0° C, (iii) power supply : AC 100 V ± 10V, 50 or 60 Hz, (iv) output : mV output of 0mV – 10mV with output resistance lower than 50Ω, mA output of 10mA –]5–0mA with maximum load resistance of 400Ω,mA output of 4 – 20mA, 2 – 10mA or 1 – 5mA selected cusualy 4 14 20mA with maximum load resistance of 800Ω.

The computer 35 employed herein is an process computer. The computer having 16 words core memory and 128 words drum memory is enough to be employed . Of course, any other suitable types may be employed in lieu of the above type.

An indicator 36 and a recorder 37 are connected to the circuit connecting the converter 34 to the computer 35. Further, another thermometer 38 is disposed in the measuring cell 18 for detecting the temperature of the circulating electrolyte. This thermometer 38 is connected to the recorder 37. The indicator 36 displays the conductivity of the circulating electrolyte, and the recorder 37 records the conductivity and the temperature of the electrolyte. Further, an operator console 39 is connected to the computer 35. The conductivity signal representative of the conductivity of the circulating electrolyte detected by the inductive solution analyzer 17 is applied to the computer 35.

In the concentration measurement with such inductive solution analyzer, it is necessary to compute both the zinc and the sulfuric acid concentration in the electrolyte. This is because of the conductivity of the electrolyte depends on the interrelation between the zinc concentration and the sulfuric acid concentration, and therefore, this conductivity is variable depending on variations of the sulfuric acid concentration even when the zinc concentration is constant. Further, even when the total zinc concentration is constant, the relation between the zinc concentration or sulfuric acid concentration and the conductivity of the electrolyte is not always linear over the entire range, and the conductivity of the electrolyte differs also from the standard conductivity of sulfuric acid. However, this relation can be substantially linearly approximated within the practical concentration range. Thus, the zinc concentration and sulfuric acid concentration can be computed on the basis of the following approximate expressions taking into account of the total zinc concentration:

$$x = A \cdot \delta + B \cdot [\,t - An\,] + C$$

$$y = D \cdot \delta + D \cdot [\,t - Zn\,] + F$$

where $x$ is the zinc concentration in the circulating electrolyte, $y$ is the sulfuric acid concentration in the circulating electrolyte, $\delta$ is the conductivity of the circulating electrolyte, $A$ to $F$ are constants, and $[t - Zn]$ is the total zinc concentration in the circulating electrolyte. This total zinc concentration $[t - Zn]$ is given by $$[t - Zn] = x + Ky$$

where K is the ratio between the atomic weight of zinc and the molecular weight of sulfuric acid.

The numerical values of the constants A to F sought by analyzing various concentration values measured by another method. These values are, for example, $A = -277.3$, $B = 0.108$ and sulfuric acid concentration computed on the basis of the basis of the approximate expressions are cyclically displayed on the operator console 39 at predetermined time intervals.

It will be understood from the foregoing detailed description of the automatic and continuous measuring system according to the present invention that the zinc and sulfuric acid concentration in the circulating electolyte can be measured with high precision by merely detecting the conductivity of the electrolyte.

The results of this automatic measuring compared with the results of the titration in Table 1.

Table 1

| No. | Zn (g/l) the results of this automatic measuring | Zn (g/l) the results of the titration | H₂SO₄ (g/l) the results of this automatic measuring | H₂SO₄ (g/l) the results of the titration | T·Zn (g/l) the results of this automatic measuring | T·Zn (g/l) the results of the titration |
|---|---|---|---|---|---|---|
| 1 | 62.41 | 62.7 | 172.5 | 178.1 | 179.8 | 181.5 |
| 2 | 58.12 | 58.4 | 182.9 | 189.7 | 183.1 | 184.9 |
| 3 | 70.04 | 70.2 | 163.4 | 167.9 | 183.1 | 182.2 |
| 4 | 62.82 | 62.0 | 175.2 | 179.0 | 183.1 | 181.5 |
| 5 | 70.85 | 69.9 | 162.1 | 167.4 | 183.1 | 181.6 |
| 6 | 62.77 | 62.0 | 176.1 | 180.5 | 183.1 | 182.4 |
| 7 | 60.80 | 60.1 | 178.6 | 179.0 | 183.1 | 179.4 |
| 8 | 60.85 | 59.8 | 178.3 | 181.4 | 183.1 | 180.7 |
| 9 | 69.39 | 68.1 | 164.5 | 168.8 | 183.1 | 180.7 |
| 10 | 61.61 | 59.8 | 177.3 | 181.4 | 183.1 | 180.8 |
| 11 | 75.25 | 75.2 | 154.9 | 155.8 | 183.1 | 179.1 |

The present invention thus solves various problems encountered in the prior art efforts to automate the preparation of electrolyte and clears the way to the desired automation of preparation of electrolyte. Further, a continuous record of electrolytic operation can be obtained since the results of measurement are recorded on the recorder.

Furthermore, the operating state can be easily controlled since the results of measurment are also displayed on the operator console through the computer.

Some examples of the present invention will now be described.

EXAMPLE 1

A part of an electrolyte circulating through an electrolytic section of a hydrometallurgical zinc production system is pumped up and fed by a diaphragm pump into the measuring cell at a flow rate of 3.0 l/min for measuring the conductivity $\delta$ ($\Omega$/cm) of the circulating electrolyte by the inductive solution analyzer having the bypass type transmitter. The detecting characteristics of this inductive solution analyzer are as follows: (i) output : DC 4mA, − 20mA, ii) measuring range : 0.2 $\Omega$/cm − 0.5$\Omega$/cm at 40°C, (iii) temperature compensation : 40° C ± 10° C. The signal representative of the detected conductivity is applied through the analog-digital converter to the electronic computer for computing the zinc and sulfuric acid concentration in the electrolyte on the basis of the approximate expressions. The converter has the following characteristics : (i) temperature compensation : temperature setting ± 10° C, (ii) ambient temperature 0° C − 40° C, (iii) power supply : AC 100V ± 10V, 50 or 60 Hz, (iv) output : mV output of 0 mV −10 mV with output resistance lower than 50$\Omega$; mA output 10 mA with maximum load resistance of 400$\Omega$; mA output of 4 mA − 20 mA with maximum load resistance of 800$\Omega$. The computer is an process computer. The approximate expressions are as follows:

TI $x$(g/1) = −277.3 · $\delta$($\Omega$/cm) + 0.108 [$t$−Zn](g/1) + 130.2

$y$(g/1) = 415.0 · $\delta$($\Omega$/cm) + 1.350 [$t$−Zn](g/1) − 197.0 where [$t$ − Zn](g/1) is the total zinc concentration and is 165 g/1 in this case.

The values of the coefficients are suitably changed when the value of [$t$ − Zn] changes from that above specified. The measuring range of the zinc concentration is about 20 to 85 g/1 with an error of about ± 0.2 g/1. The measuring range of the sulfuric acid concentration is about 130 to 220 g/l with an error of about 0.5 g/l.

Figure 6:
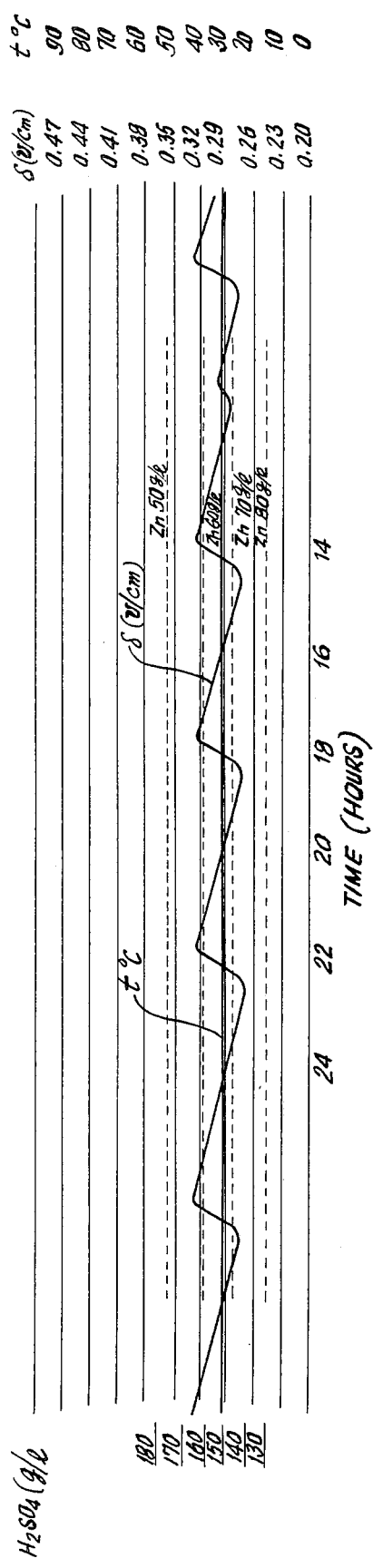
FIG. 6 and FIG. 7 are graphs showing the mark effect of automatic and continuous measurement by the system according to the present invention.

The result of conductivity measurement is shown in FIG. 6. The cycles of preparation of electrolyte and variations in the conductivity are clearly shown in this graph, and it will be seen that the conductivity can be accurately measured by the inductive solution analyzer. It will be seen further that the conductivity varies linearly in each cycle, and the result of computation of the zinc and sulfuric acid concentrations of the basis of the approximate expressions in highly reliable.

EXAMPLE 2

A part of an electrolyte circulating through an electrolytic section of a hydrometallurgical zinc production system is pumped up and fed by a diaphragm pump into the measuring cell at a flow rate of 3.0 l/min for measuring the conductivity $\delta$(/cm) of the circulating electrolyte by the inductive solution analyzer having the bypass type transmitter. The detecting characteristics of this inductive solution analyzer are the same as Example 1. The signal representative of the detected conductivity is applied through the analog-digital converter to the electronic computer for computing the zinc and sulfuric acid concentration in the electrolyte on the basis of the approximate expressions. The converter has the same characteristics as Example 2. The computer is an process computer. The approximate expressions are as follows:

$x$(g/l) = −269.36 · $\delta$(/cm) + 0.194[$t$ − Zn](g/l) + 114.39

$y$(g/l) = 439.89 · $\delta$(/cm) + 0.730 [$t$ − Zn](g/l) − 100.71 where [$t$−Zn](g/l) is the total zinc concentration and is 165 g/l in this case.

The values of the coefficients are suitably changed when the value of [$t$ = An] changes from that above specified. The measuring range of the zinc concentration is about 20 to 85 g/l with an error of about ± 0.2 g/l. The measuring range of the sulfuric acid concentration is about 130 to 220 g/l with an error of about 0.5 g/l.

Figure 7:
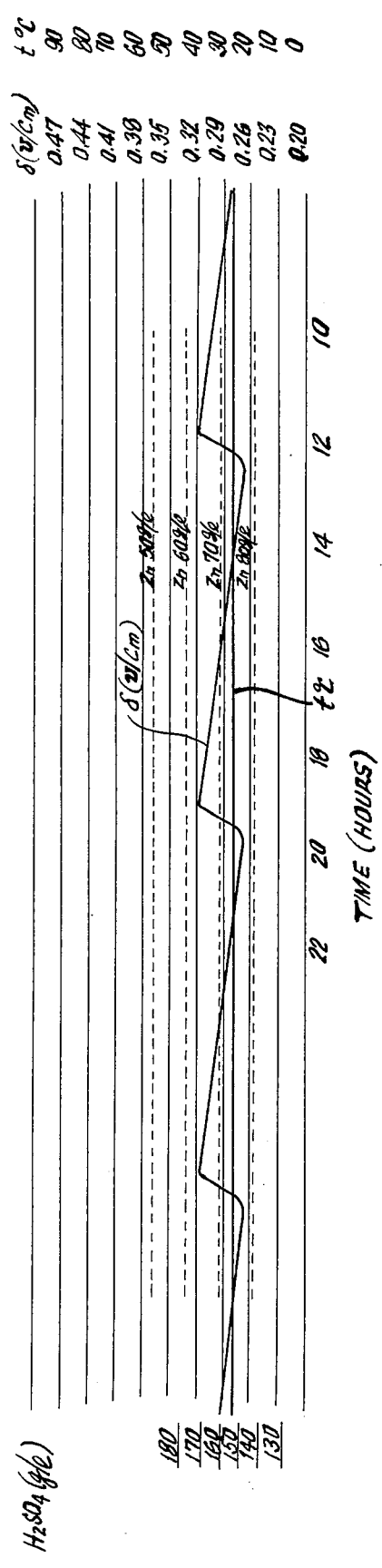

The result of conductivity measurement is shown in FIG. 7. The cycles of preparation of electrolyte and variations in the conductivity are clearly shown in this graph, and it will be seen that the conductivity can be acccurately measured by the inductive solution analyzer. It will be seen further that the conductivity varies linearly in each cycle, and the result of computation of the zinc and sulfuric acid concentrations on the basis of the approximate expressions is highly reliable.

In this Example 2, the current density is under half as much as that of Example 1, therefore the period of the times between the preparation of Electrolyte is longer than that of Example 1.

What we claim is:

1. A system for automatically and continuously measuring the zinc and sulfuric acid concentration in an electrolyte circulating through an electrolysis cell in a hydrometallurgical zinc production process, said measuring system comprising an inductive solution analyzer having a transmitter and capable of continuously detecting the conductivity of the circulating electrolyte, and a measuring cell disposed in the path of a continuous stream of the circulating electrolyte, said measuring cell comprising a defoaming chamber, a measuring chamber and an overflow chamber defined therein by a partition wall, said transmitter of said inductive solution analyzer being disposed within said measuring chamber, an overflow port formed in an upper portion of said partition wall and a first communication port bored in a middle portion of said partition wall to provide communication means between said defoaming chamber and said measuring chamber, and a second communicating port bored in a lower portion of said partition wall to provide communication means between said measuring chamber and said overflow chamber, whereby the circulating electrolyte can always flow through said measuring cell as a downward stream.

2. An automatic and continuous measuring system as claimed in claim 1, wherein the signal representative of the conductivity detected continuously by said inductive solution analyzer is applied through an analog-digital converter to an electronic computer, and said electronic computer computes automatically the zinc concentration and sulfuric acid concentration in the circulating electrolyte on the basis of predetermined approximate expressions given by $$x = A \cdot \delta + B \cdot [t - Zn] + C$$

$$y = D \cdot \delta + E \cdot [t - Zn] + F$$

where $x$ is the zinc concentration in the circulating electrolyte, $y$ is the sulfuric acid concentration in the circulating electrolyte, $\delta$ is the detected conductivity of the circulating electrolyte, $A$ to $F$ are constants, and $[t - Zn]$ is the total zinc concentration in the circulating electrolyte.

3. An automatic and continuous measuring system as claimed in claim 2, wherein the constants in the approximate expressions are respectively $A = -277.3$, $B = 0.108$, $C = 130.2$, $D = 415.0$, $E = 1.350$, and $F = -197.0$.

4. An automatic and continuous measuring system as claimed in claim 2, wherein the constants in the approximate expressions are respectively $A = -269.36$, $B = 0.194$, $C = 114.39$, $D = 439.89$, $E = 0.730$, and $F = -100.71$.

* * * * *